(12) United States Patent
Foster et al.

(10) Patent No.: US 10,272,431 B2
(45) Date of Patent: Apr. 30, 2019

(54) MICROFABRICATED CELL SORTER USING PRESSURE PULSE

(71) Applicant: Owl biomedical, Inc., Goleta, CA (US)

(72) Inventors: John S Foster, Santa Barbara, CA (US); Stefan Miltenyi, Bergische Gladbach (DE); Kevin Shields, Santa Barbara, CA (US); Mehran Hoonejani, Goleta, CA (US)

(73) Assignee: Owl biomedical, Inc., Goleta, CA (US)

( * ) Notice: Subject to any disclaimer, the term of this patent is extended or adjusted under 35 U.S.C. 154(b) by 264 days.

(21) Appl. No.: 15/436,771

(22) Filed: Feb. 18, 2017

(65) Prior Publication Data

US 2018/0236449 A1    Aug. 23, 2018

(51) Int. Cl.
| | |
|---|---|
| *G01N 15/00* | (2006.01) |
| *G01N 15/10* | (2006.01) |
| *B01L 3/00* | (2006.01) |
| *C12M 1/00* | (2006.01) |
| *G01N 15/14* | (2006.01) |

(Continued)

(52) U.S. Cl.
CPC ..... *B01L 3/502761* (2013.01); *B01L 3/50273* (2013.01); *C12M 47/04* (2013.01); *G01N 15/1459* (2013.01); *G01N 15/1484* (2013.01); *B01L 3/502715* (2013.01); *B01L 3/502738* (2013.01); *B01L 3/502776* (2013.01); *B01L 3/502784* (2013.01); *B01L 2200/0636* (2013.01); *B01L 2200/0652* (2013.01); *B01L 2300/0627* (2013.01); *B01L 2300/0864* (2013.01); *B01L 2400/043* (2013.01); *B01L 2400/0439* (2013.01); *B01L 2400/0478* (2013.01); *B01L 2400/0487* (2013.01); *B01L 2400/084* (2013.01); *G01N 2015/0288* (2013.01); *G01N 2015/1006* (2013.01); *G01N 2015/1081* (2013.01); *G01N 2015/149* (2013.01)

(58) Field of Classification Search
CPC ....... B01L 3/502761; B01L 2300/0864; B01L 2200/0652; B01L 2400/0487; B01L 3/502738; B01L 3/502776; B01L 2200/0636; B01L 2400/084; B01L 3/502715; B01L 3/50273; B01L 3/502784; G01N 2015/149; G01N 15/1459; G01N 2015/0288; G01N 2015/1081; C12M 47/04; A61M 1/3678
See application file for complete search history.

(56) References Cited

U.S. PATENT DOCUMENTS

| | | |
|---|---|---|
| 721,429 A | 2/1903 | Cutten |
| 6,838,056 B2 | 1/2005 | Foster |
| 6,941,005 B2 | 6/2005 | Lary et al. |

(Continued)

OTHER PUBLICATIONS

U.S. Appl. No. 13/374,899, filed Jan. 23, 2012, Foster, et al.
U.S. Appl. No. 13/374,898, filed Jan. 23, 2012, Foster, et al.

*Primary Examiner* — Jennifer Wecker
(74) *Attorney, Agent, or Firm* — Jaquelin K. Spong

(57) ABSTRACT

Described here is a microfabricated particle sorting device that uses a transient pulse of fluidic pressure to deflect the target particle. The transient pulse may be generated by a microfabricated (MEMS) actuator, which pushes a volume of fluid into a channel, or sucks a volume of fluid from the channel. The transient pressure pulse may divert a target particle into a sort channel.

19 Claims, 11 Drawing Sheets

(51) Int. Cl.
 *C12M 3/00* (2006.01)
 *G01N 15/02* (2006.01)

(56) References Cited

U.S. PATENT DOCUMENTS

| | | |
|---|---|---|
| 7,264,972 B2 | 4/2007 | Foster |
| 7,220,594 B2 | 5/2007 | Foster et al. |
| 7,229,838 B2 | 12/2007 | Foster et al. |
| 7,569,789 B2 | 8/2009 | Hayenga et al. |
| 7,745,221 B2 | 6/2010 | Butler et al. |
| 8,120,770 B2 | 2/2012 | Huang et al. |
| 8,186,913 B2 | 5/2012 | Toner et al. |
| 9,372,144 B2 | 6/2016 | Foster et al. |
| 2008/0261295 A1 | 10/2008 | Butler et al. |
| 2009/0014360 A1 | 1/2009 | Toner et al. |
| 2012/0292233 A1 | 11/2012 | Toner |
| 2013/0233420 A1 | 9/2013 | DiCarlo |
| 2015/0093817 A1* | 4/2015 | Foster ............... F16K 99/0046 435/288.7 |
| 2015/0268244 A1* | 9/2015 | Cho ................ G01N 15/1429 435/7.23 |
| 2015/0328637 A1* | 11/2015 | Perrault, Jr. ...... B01L 3/502738 435/287.1 |

\* cited by examiner

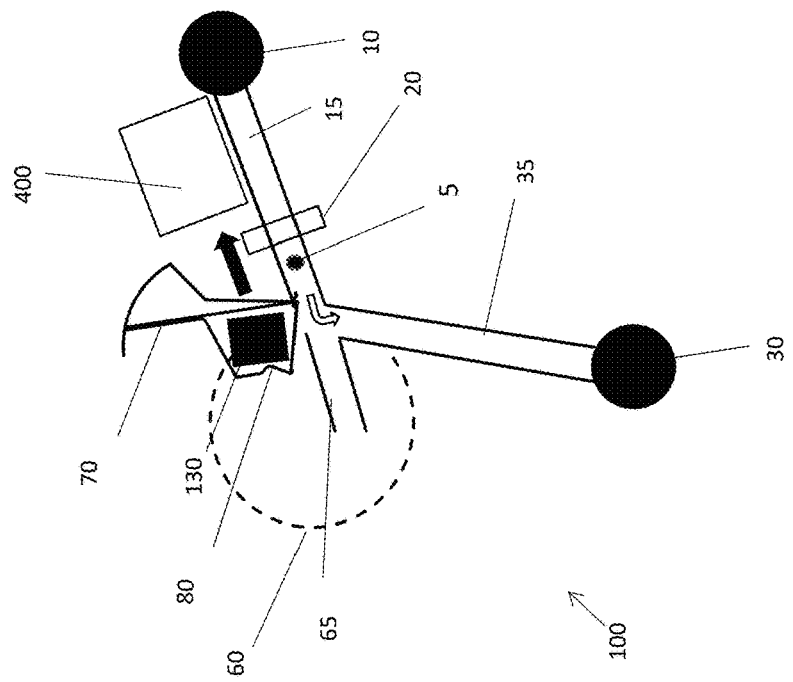
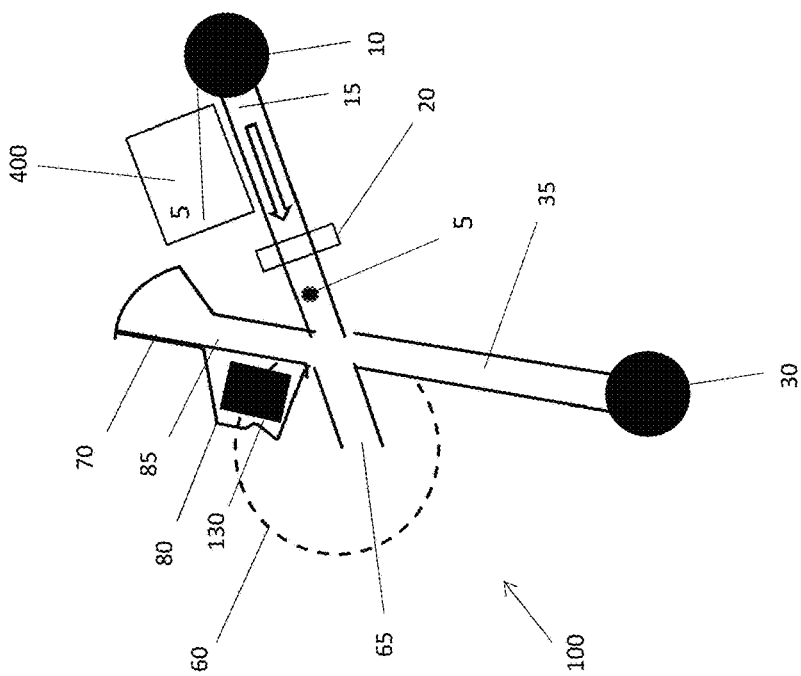

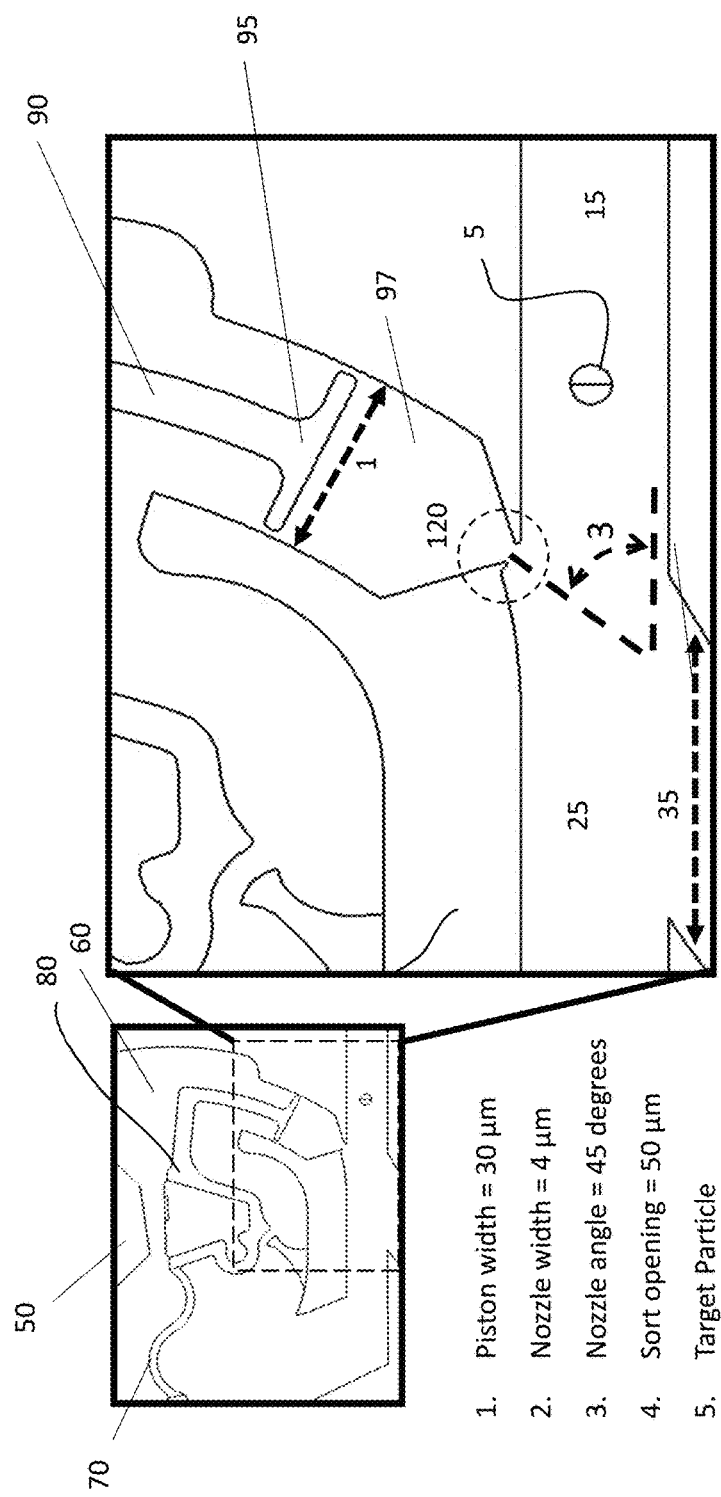

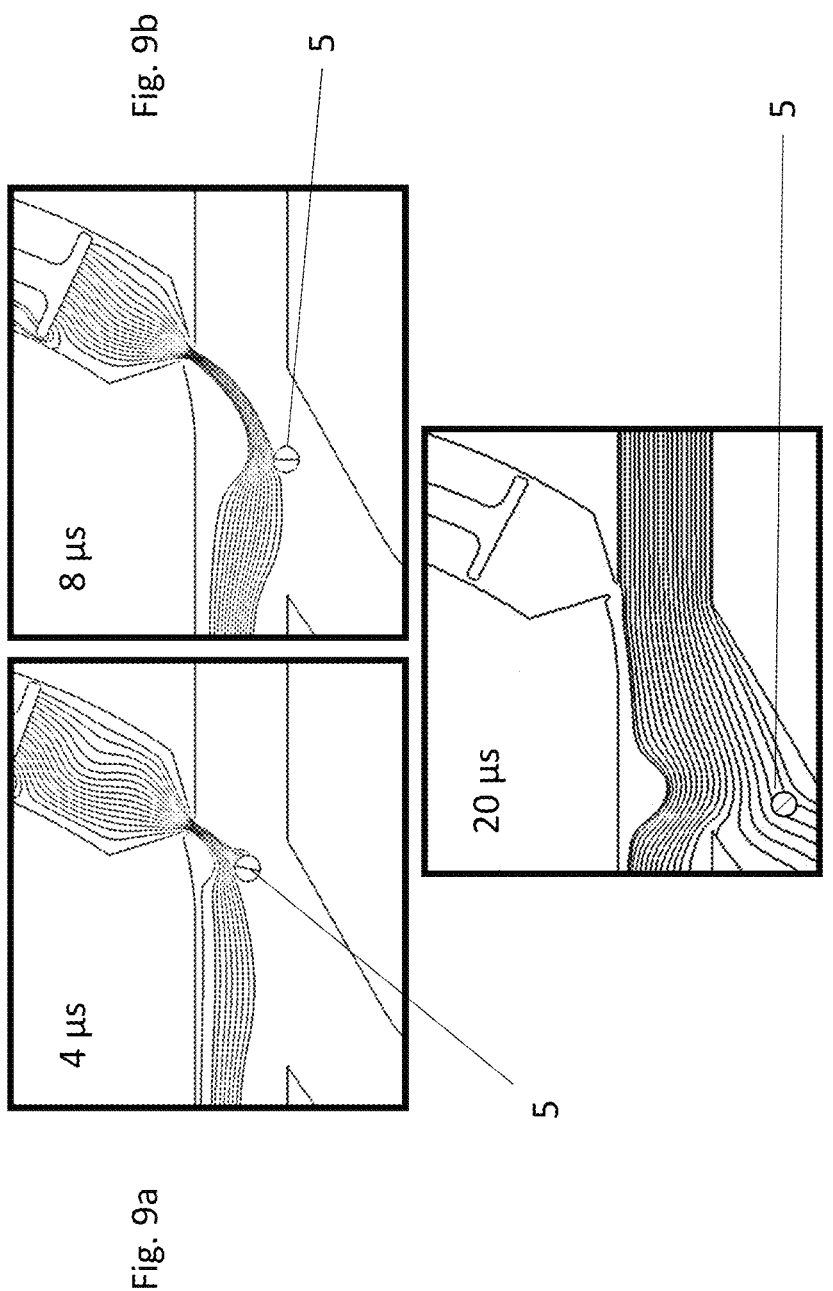

MICROFABRICATED CELL SORTER USING PRESSURE PULSE

CROSS REFERENCE TO RELATED APPLICATIONS

Not applicable.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS device may be a movable valve, used as a sorting mechanism for sorting various particles from a fluid stream, such as cells in blood or saline. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from the nozzle, the droplets are separated into different bins electrostatically, based on the fluorescence signal from the tag. Among the issues with these systems are cell damage or loss of functionality due to the decompression, difficult and costly sterilization procedures between sample, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

Because of the complexity of these devices and difficulty of manufacture, MEMS-based particle sorting devices have been slow to appear in the marketplace.

SUMMARY

Disclosed here is a particle sorting architecture which is microfabricated in nature.

The microfabricated particle sorting device may use a transient pulse of fluidic pressure to deflect the target particle. The transient pulse may be generated by a microfabricated (MEMS) actuator. In some embodiments, the microfabricated particle sorting device is electromagnetically actuated. In other embodiments, the microfabricated particle sorting device may move in one plane, and may have a sort channel and sample inlet channel in the same plane, but have the waste channel in another plane. In some embodiments, the microfabricated particle sorting device may use a negative pressure pulse to pull a target particle into the sort channel. In some embodiments, the microfabricated particle sorting device may use a positive pressure pulse to push a target particle into the sort channel. In other embodiments, the microfabricated particle sorting device may use both a positive pressure pulse and a negative pressure pulse to both push and pull the target particle into the sort channel.

The short pulse of pressurized fluid may be ejected from a narrow-orifice nozzle. The fluidic pressure pulse may be a result of the movement of a structure microfabricated on the substrate. The forcing, or actuation means, may also be fabricated on the substrate. The actuation force may be electrostatic, piezo-electric or electromagnetic, for example. In contrast to prior art devices, the force generating and moving mechanism is formed using microfabricated means, directly on a semiconductor substrate. Accordingly, the forcing structure may be an integral part, and may be formed directly on, the same fabrication substrate as the microfluidic channels through which the sample stream flows. Also, the sorting is done hydrodynamically, rather than mechanically, where a fluid pressure pulse rather than a mechanical flow diverter moves the particle into the sort channel. Hydrodynamic forces are likely to be gentler and more reliable than mechanical sorting.

More generally, the microfabricated particle sorting device may be fabricated on a substrate, wherein the microfabricated particle sorting device separates a target particle from non-target material flowing in a fluid stream. The particle sorting device may include a detection region which generates a signal distinguishing the target particle from non-target material, a sample inlet channel, a sort channel and a waste channel also fabricated on the same substrate, wherein a target particle is urged into the sort channel rather than the waste channel by a transient pulse of fluidic pressure; wherein the pulse of pressure is generated by an actuator fabricated on the same substrate as the sample inlet channel.

BRIEF DESCRIPTION OF THE DRAWINGS

Various exemplary details are described with reference to the following figures, wherein:

FIG. 1a is a schematic illustration of a microfabricated pressure pulse generating sorting device in the quiescent position; FIG. 1b is a schematic illustration of a microfabricated particle sorting device in the actuated position;

FIG. 8 shows additional detail of the embodiment shown in FIG. 7;

FIG. 9a-9c show streamlines of the flow through the sample channel as the actuator moves;

It should be understood that the drawings are not necessarily to scale, and that like numbers may refer to like features.

DETAILED DESCRIPTION

Figure 2:
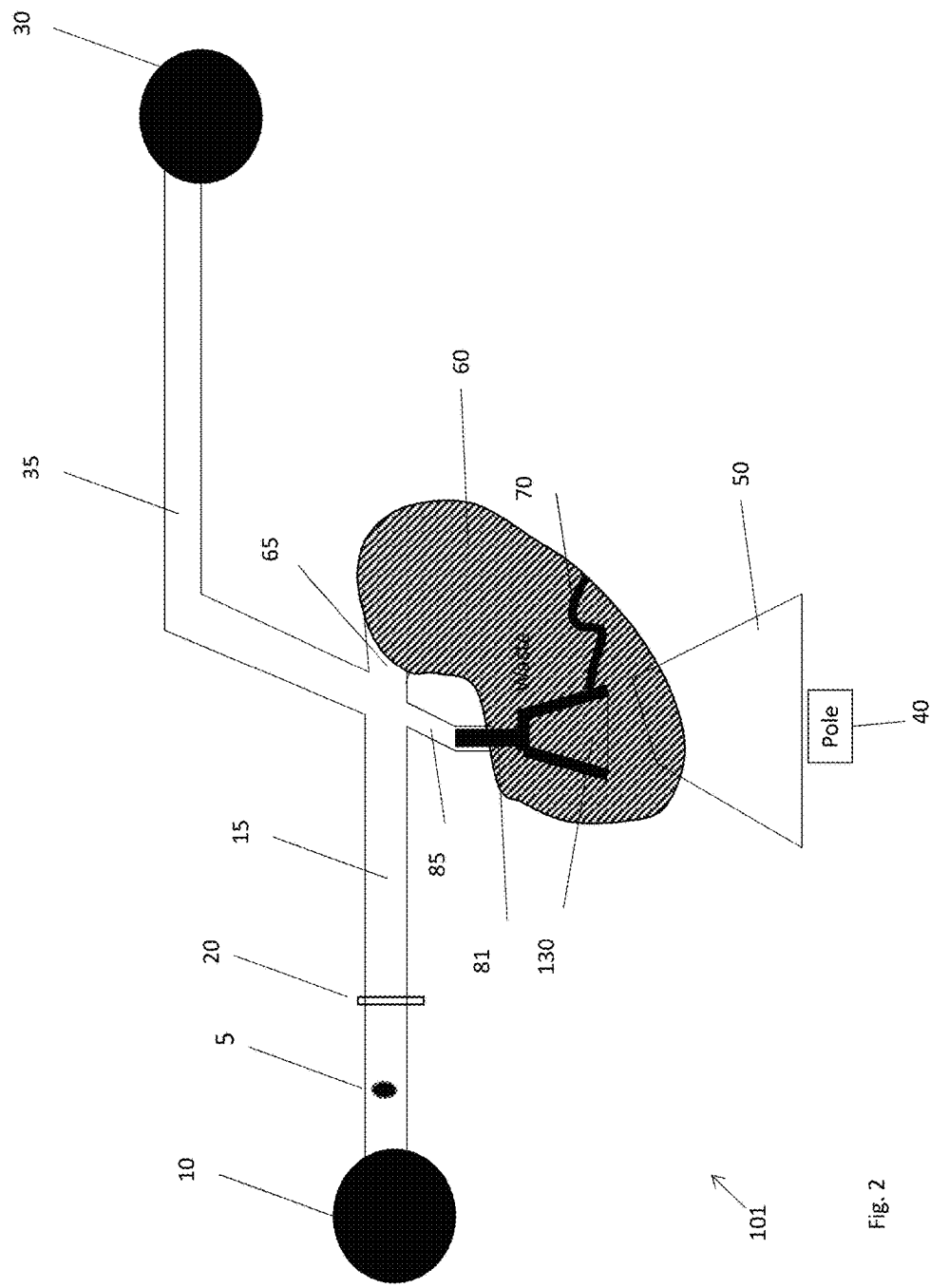
FIG. 2 is an embodiment of a particle sorting system which sorts particles using a positive pulse of fluidic pressure, which is exerted when the actuator is released.

A particle manipulation system is described that separates a target particle form non-target material in a sample stream, by applying a transient pressure pulse to the target particle and diverting its trajectory from a waste channel into a sort channel. In the exemplary embodiments described below, an actuator formed in a substrate is caused to move by the exertion of a force on the actuator. The movement is applied to a fluid column, causing a transient pressure pulse to be generated in the fluid. This pressure pulse, either positive or negative pressure pulse, may alter the trajectory of a target particle flowing in a sample stream past the actuator. The mechanism for generating the transient pressure pulse may be fabricated on the same substrate as the channels in which the sample fluid flows.

A sample stream containing at least one target particle as well as non-target material may be introduced to the device from a sample reservoir to a sample inlet channel. The sample inlet channel may pass through a query zone, wherein a detector may detect the presence of a target particle. Upon detection of a target particle in the query zone, a controller may direct a force generating structure to generate a force to move the movable member of the actuator. Movement of the actuator may generate the transient pressure pulse, directing the target particle from the waste stream into the sort stream and then on to the sort reservoir. In some embodiments, the transient pressure pulse may be positive, pushing the target particle into the sort channel. In other embodiments, the transient pressure pulse may be negative, pulling the target particle into the sort channel. In some embodiments, the target particle is sorted with the actuator is actuated (normally closed). In other embodiments, the target particle is sorted with the actuator is released from actuation (normally open).

In some embodiments, the transient pressure pulse is applied at an angle to the centerline of the sample stream. The angle may be between about 30 degrees and 60 degrees, but is generally less than 90 degrees (substantially less than orthogonal) to the centerline of the sample stream. The transient pressure pulse may be formed by a nozzle disposed at an angle with respect to the centerline of the channels.

The actuation means may be electromagnetic, wherein an electromagnet, separate and external to the substrate supporting the fluid channels and actuator produces magnetic flux in the vicinity of the actuator. A magnetically permeable feature in the substrate and in the actuator may interact with the electromagnet, causing the actuator to move. The movement of the actuator may create the transient pressure pulse, forcing fluid to flow in a channel, and divert the target particle from a nominal path into a waste reservoir, into another sort channel path and sort reservoir.

The following discussion presents a plurality of exemplary embodiments of the novel particle manipulation system. The following reference numbers are used in the accompanying figures:

100-106 pressure sorting device embodiments
5 target particle
10 the sample reservoir
15 the sample channel
20 laser query region
30 the sort reservoir
35 sort channel
60 waste channel/reservoir
65 waste output channel
50 permeable feature
55 permeable feature
40 magnetic pole
45 pole
85 transient pressure region/pressure channel
70 restoring spring
75 restoring spring
80 movable member
82 movable member
90 lever arm
95 pistons
97 piston pressure channel
120 nozzle
2 nozzle (FIG. 8)
3 angle piston/inlet channel
130 permeable feature
400 electromagnet/force generating apparatus FIG. 1a is a plan view illustration of a microfabricated fluidic pressure sorting device 100 in the quiescent (unactuated) position. The pressure sorting device 100 may include a microfabricated movable member 80 and a number of microfabricated fluidic channels 15, 35 and 65. The movable member 80 and microfabricated fluidic channels 15, 35 and 65 may be formed in a suitable substrate, such as a silicon substrate, using MEMS lithographic fabrication techniques as described in greater detail below. The fabrication substrate may have a fabrication plane in which the device is formed and in which the movable member 80 moves. As described further below, the microfabricated inlet channel 15 and sort channel 35 may also lie in this plane.

A sample stream may be introduced to the pressure sorting device 100 by a sample inlet channel 15 leading from a sample reservoir 10. The sample stream may contain a mixture of particles, including at least one desired, target particle 5 and a number of other undesired, non-target particles. The particles may be suspended in a fluid. For example, the target particle 5 may be a biological material such as a stem cell, a cancer cell, a zygote, a protein, a T-cell, a bacteria, a component of blood, a DNA fragment, for example, suspended in a buffer fluid such as saline.

The inlet channel 15 may be formed in the same fabrication plane as the movable member 80, such that the flow of the fluid is substantially in that plane. The motion of the movable member 80 may also be within this fabrication plane.

The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature. However, other sorts of distinguishing signals may be used, including scattered light or side scattered light which may be based on the morphology of a particle, or any number of mechanical, chemical, electric or magnetic effects that can identify a particle as being either a target particle 5, and thus sorted or saved, or a non-target particle and thus rejected or otherwise disposed of.

With the movable member 80 motionless and in the position shown in FIG. 1a, the input stream may pass unimpeded to an output channel 65 and waste reservoir 60, respectively, which may be out of the plane of the inlet channel 15, and thus out of the fabrication plane of the pressure sorting device 100. That is, the flow is from the inlet channel 15 to the output channel 65, from which it flows substantially vertically into the waste output reservoir 60. Thus, the flow to the waste reservoir 60 from the inlet channel 15 is substantially orthogonal. In other words, this short output or waste channel 65 may lead to an out-of-plane waste channel reservoir 60 that may be perpendicular to the plane of the paper shown in FIG. 1a. In some embodiments, the waste channel 65 is exceedingly short, so that the input channel 15 flows essentially directly into the vertical waste reservoir 60. More generally, the output channel 65 may not be parallel to the plane of the inlet channel 15 or sort channel 35, or the fabrication plane of the movable member 80, or in its plane of motion.

The output or waste channel reservoir 60 may be a hole formed in the fabrication substrate, or in a covering substrate that is bonded to the fabrication substrate. The contour of the orifice between the waste channel 65 and the waste channel reservoir 60 may be such that it overlaps some, but not all, of the inlet channel 15 and sort channel 35. By having the contour of the vertical hole overlap the inlet channel, a route may exist for the input stream to flow directly into the waste orifice 60 when the movable member 80 is motionless.

FIG. 1b is a plan view of the microfabricated pressure sorting device 100 in the actuated position. In this position, the movable member 80 is deflected into the position shown in FIG. 1b. The sort output channel 35 may lie in substantially the same plane as the inlet channel 15, such that the flow within the sort channel 35 is also in substantially the same plane as the flow within the inlet channel 15. However, as discussed further below, the sort channel 35 may be disposed at a non-orthogonal angle with respect to the sample inlet channel 15.

Actuation of movable member 80 may arise from a force from force-generating apparatus 400, shown generically in FIG. 1b. In some embodiments, force-generating apparatus 400 may be an electromagnet, however, it should be understood that force-generating apparatus may also be electrostatic, piezoelectric, or some other means to exert a force on movable member 80, causing it to move from a first position (FIG. 1a) to a second position (FIG. 1b).

When the movable member 80 moves from the position shown in FIG. 1a to the position shown in FIG. 1b, it may force fluid out of the pressure channel 85 and into the sample stream 15. The pressure channel 85 is generally the microfabricated channel that accepts the positive (or negative) transient fluid pressure pulse. This may cause a transient increase in the fluid pressure at the outlet of the channel 85. This transient pressure pulse may redirect the target particle 5 from the sample-to-waste stream and into the sample-to-sort channel 35.

It should be understood that although channel 35 is referred to as the "sort channel" and orifice 60 is referred to as the "waste orifice", these terms can be interchanged such that the sample stream is directed into the waste channel 65 and the waste stream is directed into sort channel 35, without any loss of generality. Similarly, the "inlet channel" 15 and "sort channel" 35 may be reversed. The terms used to designate the three channels are arbitrary, but the inlet stream may be diverted by the valve 80 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

The movable member or valve 80 may be attached to the substrate with a flexible spring 70. The spring 70 may be a narrow isthmus of substrate material. In the example set forth here, the substrate material may be single crystal silicon, which is known for its outstanding mechanical properties, such as its strength, low residual stress and resistance to creep. With proper doping, the material can also be made to be sufficiently conductive so as to avoid charge build up on any portion of the device, which might otherwise interfere with its movement. The spring 70 may have a serpentine shape as shown in FIG. 2, having a width of about 1 micron to about 10 microns and a spring constant of between about 10 N/m and 100 N/m, and preferably about 40 N/m.

Also shown in the microfabricated embodiment of FIGS. 1a and 1b is a magnetically permeable feature 130 which may be inlaid into the movable member 80. This magnetically permeable feature may interact with a source of magnetic flux being produced adjacent and near to the permeable feature 130. The permeable feature 130 may be nickel iron permalloy, for example, which is a highly permeable ferromagnetic material well known to those of ordinary skill in the art. Permalloy is typically about 50-80% nickel and 40-20% iron. 55/45 is a common magnetically permeable alloy. The NiFe may be sputter deposited and planarized after the deposition. This material inlay may occur before the movable member 80 is released from the substrate. Exemplary fabrication techniques are disclosed in U.S. Pat. No. 9,372,144 issued Jun. 21, 2016, which is hereby incorporated by reference in its entirety.

Many embodiments also have a stationary permeable magnetic feature 50 embedded into the substrate. Permeable feature 50 is distinct from permeable feature 130, because it remains stationary on the substrate whereas permeable feature 130 moves with the movable member in which it is inlaid. The purpose of the stationary magnetic feature 50 may be to focus the magnetic lines of flux which are diverging from the north pole of the electromagnet 400, and concentrated them in the region of the movable member 80. This serves to enhance the gradient of the magnetic field and thus enhance the magnetic force, and thus the speed, of the movable member 80.

The source of magnetic flux may be an electromagnet, which may be a conductive coil wrapped around another magnetically permeable core. The design of a suitable electromagnet is disclosed in U.S. patent application Ser. No. 14/634,909, filed Mar. 2, 2015.

Accordingly, an external source of magnetic field lines of flux may be provided outside the pressure sorting device 100. This source may be an electromagnet 400. The electromagnet 400 may include a permeable core around which a conductor is wound. The wound conductor or coil and core generate a magnetic field which exits the pole of the magnet, diverges, and returns to the opposite pole, as is well known from electromagnetism. Accordingly, the movable member 80 is generally drawn toward the pole of the electromagnet 400 as shown in FIG. 1b.

When the electromagnet 400 is quiescent, and no current is being supplied to coil, the restoring force of spring 70 causes the movable member 80 to return to the position shown in FIG. 1a. In this position, the inlet stream passes unimpeded through the device to the waste channel 65. This position is shown in FIG. 1a. When the electromagnet 400 is activated, and a current is applied through the coil, a magnetic field arises in the core and exits the pole of the core. These poles have reference number 40 associated with them throughout the FIGS. 1-7. As mentioned previously, the permeable portion 130 of the movable member 80 is drawn toward the electromagnet 400, thus moving the movable member 80 such that the inlet stream in inlet channel 15 is redirected by a transient fluid pressure pulse to the sort channel 35. This position is shown in FIG. 1b.

Among the distinguishing features of the particle pressure sorting device 1, is the non-orthogonal angle between the sort channel 35 and the sample input channel 15. Similarly, there may be an acute angle between pressure channel 85 and sample input channel 15.

Another distinguishing feature is that the means for causing the pressure pulse is a structure which is on board the substrate. In other words, the movable member and actuator 80 may be microfabricated on a substrate. The means for moving this movable member or actuator 80 may be fabricated on board this same substrate.

Another distinguishing feature is that the actuation means may be electromagnetic, wherein the motion is caused by a magnetostatic interaction between a magnetically permeable feature 130 and a separate, electromagnet 400 which is not directly attached to this same substrate.

Another distinguishing feature of the microfabricated cell sorter using a transient pressure pulse is the out-of-plane waste channel 60, which has advantages that are described later especially with respect to FIG. 6.

It should be understood, however, that these advantageous features may not be found in all embodiments, and that the presence, or absence thereof, does not define the scope of the invention. Instead, the scope is defined by the appended claims.

FIG. 2 is a schematic illustration of a microfabricated particle sorting device 101 using a pressure pulse. In this embodiment, a transient positive pressure pulse may deflect the target particle when the movable member is released, rather than actuated.

In FIG. 2, as was the case in the embodiment of FIGS. 1a and 1b, and as may be the case with the embodiments to follow, the sample stream may enter from the sample input reservoir 10, flow down the input channel 15, and pass the laser query zone 20. As mentioned previously, the particles may be queried by a laser irradiation. Desired target particles may fluoresce upon irradiation, because of the presence of a fluorescent tag bound to the target particle. From the presence or lack of fluorescence, it may be determined that either a target particle 5 or non-target material, is passing through the input channel 15. In the event that a target particle 5 is detected, the computer may send a sort pulse to the actuator. The computer may energize the electromagnet 400, causing the permeable material 130 to be drawn toward the electromagnet 400. The motion (either at actuation or at release from actuation) of the movable member 80 may cause a transient pressure pulse to occur in the pressure channel 85. The pressure pulse may urge the target particle into the sort channel 35 and eventually into the sort reservoir 30, rather than into the waste channel 65 and waste reservoir 60.

Among the distinguishing features of the pressure sorter 101 is that the transient positive pressure pulse may deflect the target particle when the movable member is released, rather than actuated. Depicted schematically is a plunger-type actuator 81 rather than a flap-type actuator 80 as was illustrated in FIGS. 1a and 1b. As before, a magnetically permeable material 130 may be inlaid into the movable plunger 81, and drawn toward a permeable feature 50 fabricated on the substrate.

Because of this magnetostatic interaction, when an electromagnet 400 is energized, the plunger 81 will be drawn toward the permeable feature 50, thus sucking fluid into the channel 85 and causing a transient negative pressure pulse to occur in the sample channel. When the negative transient has subsided, the electromagnet 400 may be de-energized, causing the plunger 81 to return to its original position, because of the restoring force provided by the restoring spring 70. This movement may create a positive fluidic pressure transient in the pressure channel 85, which may deflect the target particle 5 into the sort channel 35.

Accordingly, upon detection of a target particle in the sample channel 35, the actuator 400 may be energized, drawing the plunger 81 down by generating magnetic flux at pole 40. After the particle has passed from the laser query region 20 and arrived at the intersection point of the sort channel 35 and the waste channel 65, the plunger 81 may be released to sort the target particle 5, by the transient positive pressure pulse.

Accordingly, the control algorithm for pressure sorter 101 may be to apply a current pulse well before the target particle appears at the opening of pressure channel 85, and to de-energize the electromagnet to sort. Alternatively, the plunger 81 may generally be held in the retracted position bay applying current to the electromagnet in general. The plunger 81 may then be released to sort.

An important design consideration may be the relative fluidic resistance between the sort channel 35 and the waste channel 65. In general, the sort path 35 may have a fluid resistance which is about 3× that of the waste path 65. A substantial fluid flow along both the sort channel and the waste channel may be required to allow the transient pressure pulse to operate effectively on the vector pointed along the fluid flow. Particles may be centered in the inlet channel and would normally flow to the waste orifice unless the sorting apparatus actuates and pushes a target particle towards the sort channel. This centering may be accomplished by a microfabricated fluidic manifold to focus the particles in a certain area within the fluid stream. The manifold may include a sample inlet and sheath fluid channel. The combined fluid may then flow around a focusing element coupled to the inlet channel, here a z-focusing channel, which tends to herd the particles into a particular plane within the flow. The combined fluid may then pass another intersection point, a "y-intersection point", which introduces additional sheath fluid above and below the plane of particles. At the y-intersection point, two flows may join the z-focus channel 330 from substantially antiparallel directions, and orthogonal to the z-focus channel 330. This intersection may compress the plane of particles into a single point, substantially in the center of the stream. Focusing the particles into a certain volume tends to decrease the uncertainly in their location, and thus the uncertainty in the timing. Such hydrodynamic focusing may therefore improve the speed and/or accuracy of the sorting operation.

As can be seen from FIG. 2, the waste channel 65 may be quite short, and may be in fluid communication with a larger, vertical flow channel with exceedingly low fluid resistance. This may be an important design feature because the fluid pressure on the backside of the movable member 80 may be a limiting factor on the speed with which it can be actuated, and thus on the speed of the sorter. By minimizing this back pressure, the speed of the device may be increased. By having the movable member 80 in fluid communication with low fluid resistance with this large volume of fluid may minimize the back pressure and thus maximize the sorting speed. Additionally, lowering the back pressure to the backside of the movable member may reduce disturbances to the inlet flow caused by actuation. The reduction of flow disturbance is especially important in high sort rate applications.

The waste orifice 60 may be disposed generally orthogonal to the fabrication plane, that is, orthogonal to the sample channel 15 and sort channel 35, and orthogonal to the plane of motion of the movable member 80 and 81. These features, while they are not necessary to the scope of the invention, and the invention should not be interpreted to be limited to these features, these features may be in common among the embodiments described here.

Figure 3:
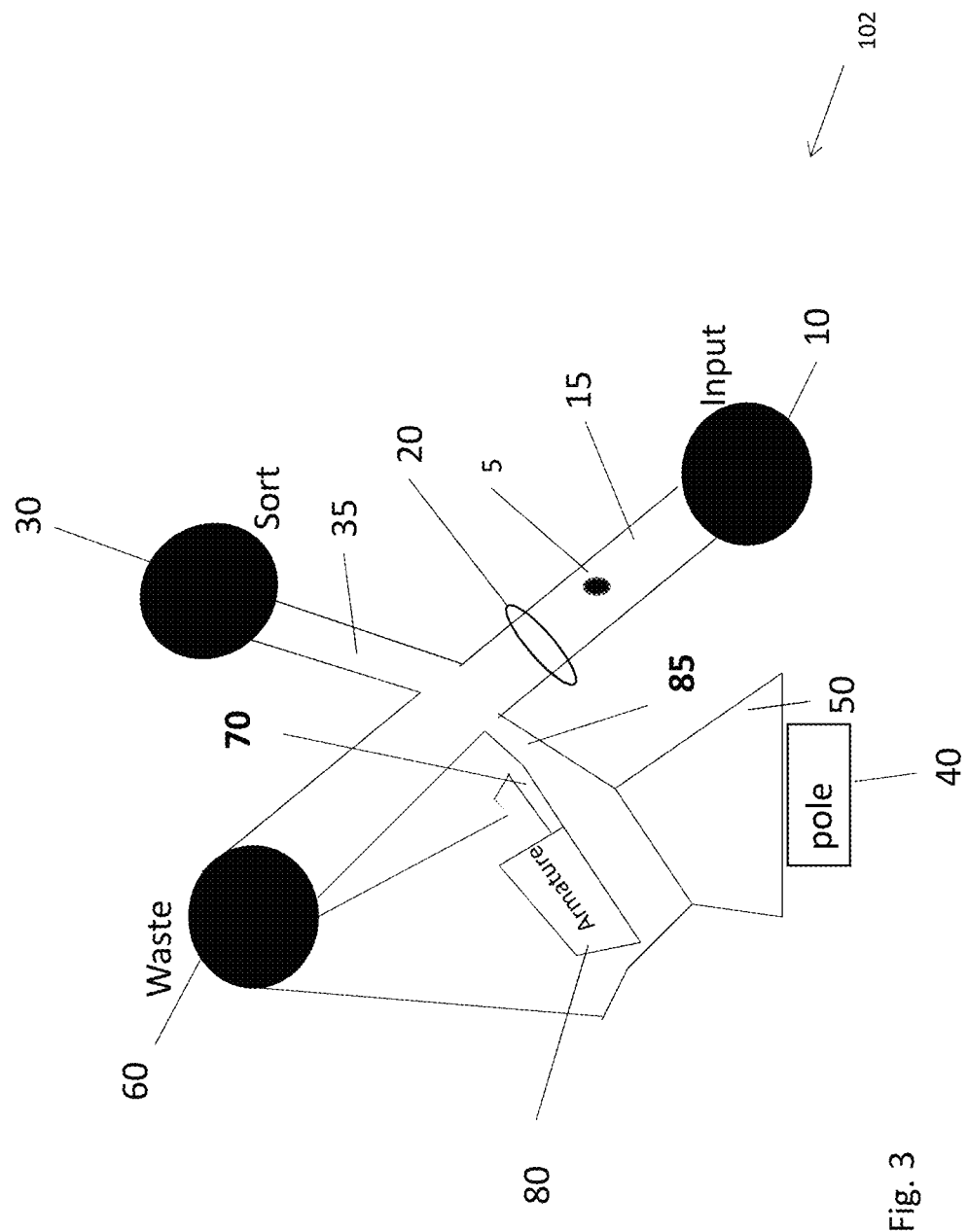
FIG. 3 is an embodiment of a particle sorting system which sorts particles using a positive pulse of fluidic pressure when the device is actuated.

FIG. 3 shows another embodiment 102 of the transient pressure sorter. In the embodiment shown in FIG. 3, the sorter may sort upon actuation of the movable member 80, rather than its release from actuation as in embodiment 101 of FIG. 2.

In the embodiment 102 shown in FIG. 3, the sample stream may again enter from the input reservoir 10, flow down the input channel 15, and pass the laser query zone 20. The particles are queried by a laser irradiating them. Desired target particles 5 may fluoresce upon irradiation, because of the presence of a fluorescent tag bound to the target particle. From the presence or absence of fluorescence, it may be determined that either a target particle or non-target material is passing through the input channel 15. In the event that a target particle is detected, the computer will once again send a sort pulse to the actuator. That will cause the sort function to take place.

The sort function for embodiment 102 may be the retraction of movable member 80, forcing pressurized fluid into the pressure channel 85. This pulse of pressure may redirect a target particle 5 from the sample channel 15 into the sort channel 35. From the sort channel 35, the target particle may be stored in a sort reservoir 30. Once again, the actuation means may be electromagnetic, wherein the movable member 80 is attracted magnetostatically to a diverging source of magnetic flux.

The permeable feature 50 may be inlaid into the substrate, and may interact with an external electromagnet 400. When the electromagnet 400 is activated, the flux emanating from the core and then from the permeable feature 50 draws the permeable movable member 80 towards it, causing the spring 70 to flex. When the electromagnet is quiescent, the spring returns the movable member 80 to its original position, as was illustrated in FIGS. 1a and 1b.

The pressure pulse in pressure channel 85 may urge the target particle 5 into the sort channel 35 disposed on the opposing side of the sample channel 15.

Figure 4:
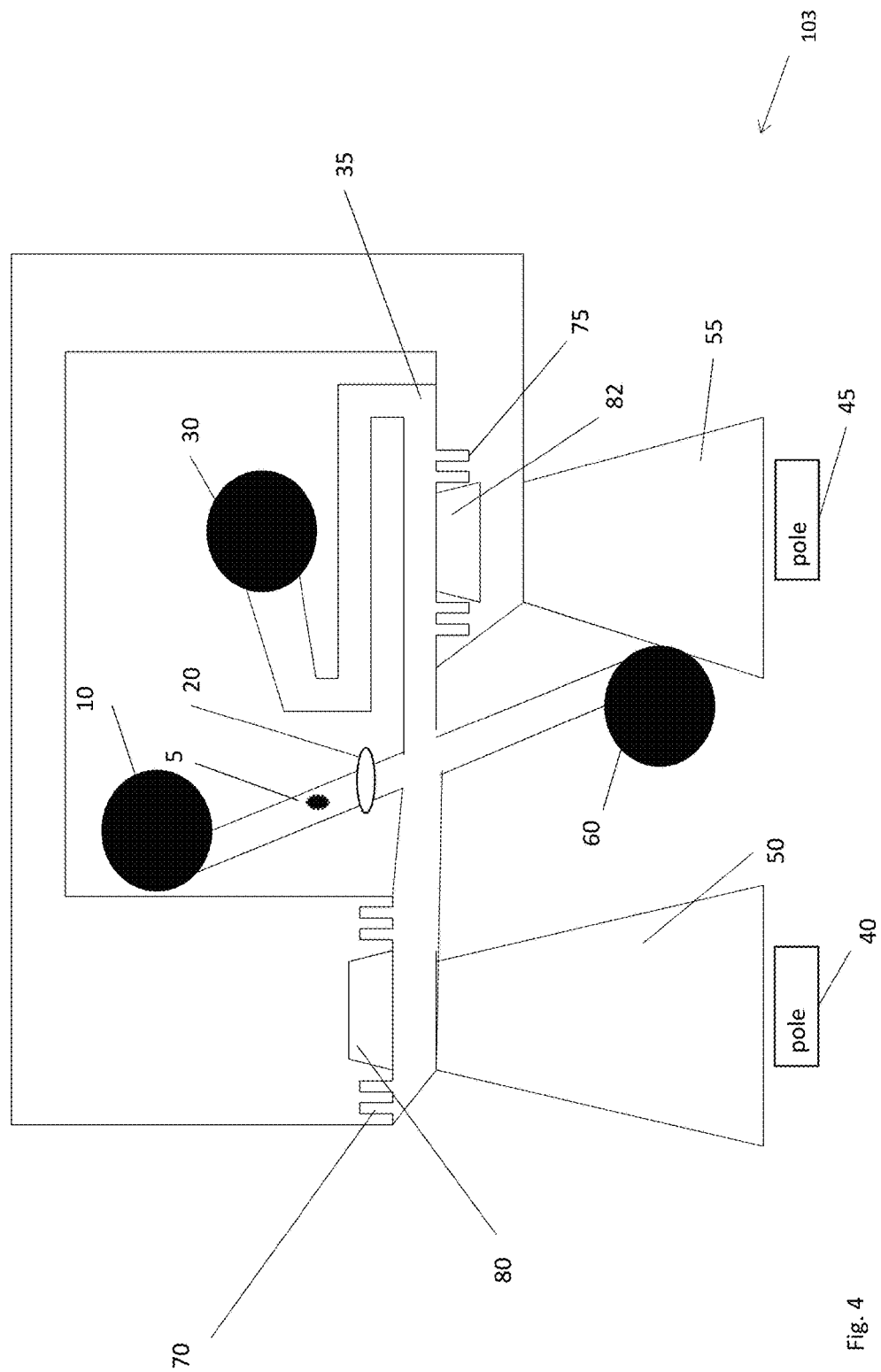
FIG. 4 is an embodiment of a particle sorting system which sorts particles using a pulse of fluidic pressure, using positive and negative pressure.

FIG. 4 shows another embodiment 103 of a particle sorting device using a transient pressure pulse. A distinguishing feature of this embodiment is that the transient pressure pulse is both positive and negative, that is, one movable member 80 pushes the target particle 5 with a positive pressure pulse, while another movable member 82 pulls the target particle 5 with a negative pressure pulse.

In the embodiment 103 shown in FIG. 4, the sample stream may again enter from the input reservoir 10, flow down the input channel 15, and pass the laser query zone 20. The particles may be queried by a laser irradiating them. Desired target particles 5 may fluorescence upon irradiation, because of the presence of a fluorescent tag bound to the target particle 5. From the presence or lack of fluorescence, it may be determined that either a target particle 5 or non-target material, is passing through the input channel 15. In the event that a target particle 5 is detected, the computer will once again send a sort pulse to the actuator. That will cause the sort function to take place.

Depending on the signal, a computer may determine that the target particle 5 exists within the channel, and that should be sorted. In this event, the computer may send a signal to a current generating device which may cause current to flow through a coil of an electromagnet 400 (not shown). This electromagnetic cores 40 and 45 will produce magnetic flux which enters the permeable features 50 and 55. The flux then exits from the tip of the features 50 and 55, and in the far field returns to the south pole of the electromagnet.

As a result of the generation of this magnetic flux, movable members 80 and 82 are drawn toward their respective permeable polls 50 and 55. Movable members 80 and 82 may cause a pressure pulse (positive for movable member 80, negative for movable member 82) to be applied to the sample stream, the positive pressure pulse from movable member 80 pushing the fluid and target particle 5, and the negative pressure pulse from movable member 82 pulling the sample fluid and target particle 5. However both pressure pulses tend to urge a target particle 5 into the sort channel 35, and eventually into the sort reservoir 30. It should be understood that the particle sorting device 100-106 using a transient pressure pulse may either push a target particle 5 into the sort channel 35, or pull a target particle 5 into the sort channel 35, or both push and pull a target particle 5 into the sort channel 35. As with the other embodiments, restoring springs 70 and 75 may return the movable member 80 and 82 to their original positions.

Accordingly, the embodiment 103 shown in FIG. 4 maybe of the "push-pull" type, wherein one movable member 80 is pushing while the other movable member 82 is pulling fluid into the channel. 35. Using the embodiment shown in FIG. 4, the pushing movable member 80 and the pulling movable member 82 may both the actuated by a single electromagnetic coil (not shown in FIG. 4). Accordingly, in some embodiments, the movable members 80 and 82 may both be actuated by a single electromagnetic coil, which is disposed on one side of the device 103. The electromagnet 400 may be situated outside the boundaries of the substrate itself, which contains the rest of the structure, including the magnetically permeable poles 50 and 55. Accordingly, the force generating means 400, which in some embodiments, may be understood to be the electromagnet motor, may be mechanically unattached to the substrate that supports the rest of the mechanism.

As can be seen in FIG. 4, the push-pull configuration may be configured to move a volume of fluid back and forth within an enclosed channel. This may have advantages in terms of allowing a smaller volume of fluid to be moved, such that fluid resistance is minimized and sort speed is maximized. Also, inlet flow disturbances may be reduced.

Figure 5:
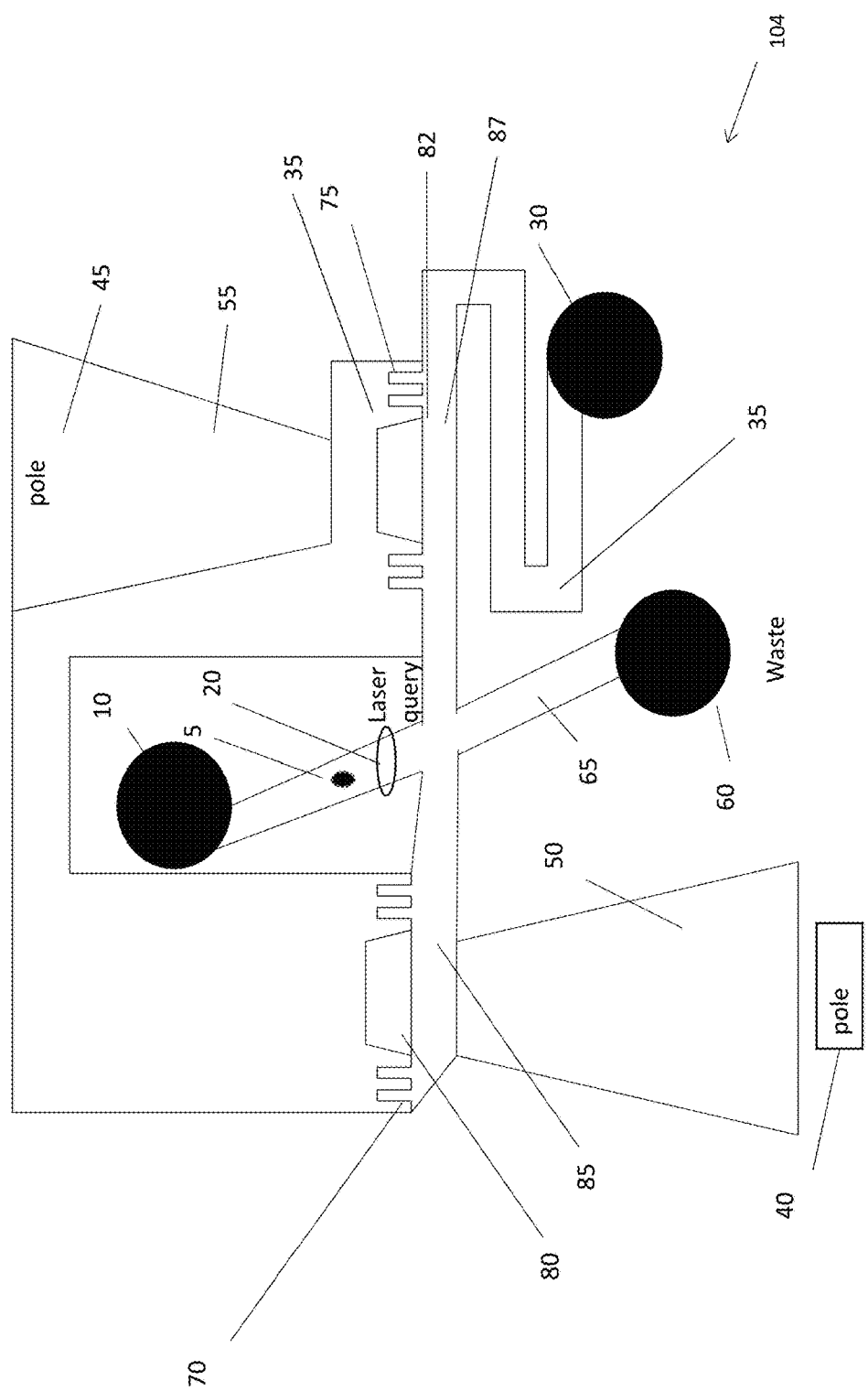
FIG. 5 is an embodiment of a particle sorting system which sorts particles using a pulse of fluidic pressure wherein the amount of dead volume is reduced.

FIG. 5 shows another embodiment 104 of a particle sorting device using a transient pressure pulse. A distinguishing feature of this embodiment is that the volume of fluid that is exchanged by the pushing movable member (80) and the pulling movable member (82) is substantially smaller than in the previous embodiment shown in FIG. 4.

The embodiment 104 shown in FIG. 5 is similar to the embodiment shown in FIG. 4, in that it is also a push-pull type of actuation mechanism. As before, in the embodiment shown in FIG. 4, the sample stream may enter from the input reservoir 10, flow down the input channel 15, and pass the laser query zone 20. The particles are queried by a laser irradiating them. Desired target particles 5 may fluoresce upon irradiation, because of the presence of a fluorescent tag bound to the target particle 5. From the presence or lack of fluorescence, it may be determined that either a target particle 5 or non-target material, is passing through the input channel 15. In the event that a target particle 5 is detected, the computer will once again send a sort pulse to the actuator. That will cause the sort function to take place.

When the sort pulse is applied to the electromagnet, the movable member 80 may be drawn toward the permeable feature 50, forcing fluid to the right and forming a high-pressure transient fluid pressure region 85 at the entrance to the sort channel. This high pressure pulse tends to push the target particle 5 into the sort channel 35. At the same time, the pulling movable member 82 may interact with permeable feature 55, and so will be drawn toward the permeable pole 55, which will suck the fluid further along the sort channel 35. This low pressure pulse tends to pull the target particle 5 into the sort channel 35. As the flow continues, the target particle 5 will eventually flow into the sort reservoir 30.

One different aspect of the embodiment 104 shown in FIG. 5 compared to the embodiment 103 shown in FIG. 4, is that the electromagnets which drive a magnetic field in permeable features 50, and 52 may be required to be on opposite sides of the chip. That is, one electromagnet may be disposed at the bottom of the figure, where is the other electromagnet may need to be disposed of the top of the figure. This may present a difficult manufacturing problem. However, the "dead" volume with the fluid pressure channels may be smaller in this embodiment 104 than in embodiment 103 shown in FIG. 4, because of the shorter path between 80 and 82.

Figure 6:
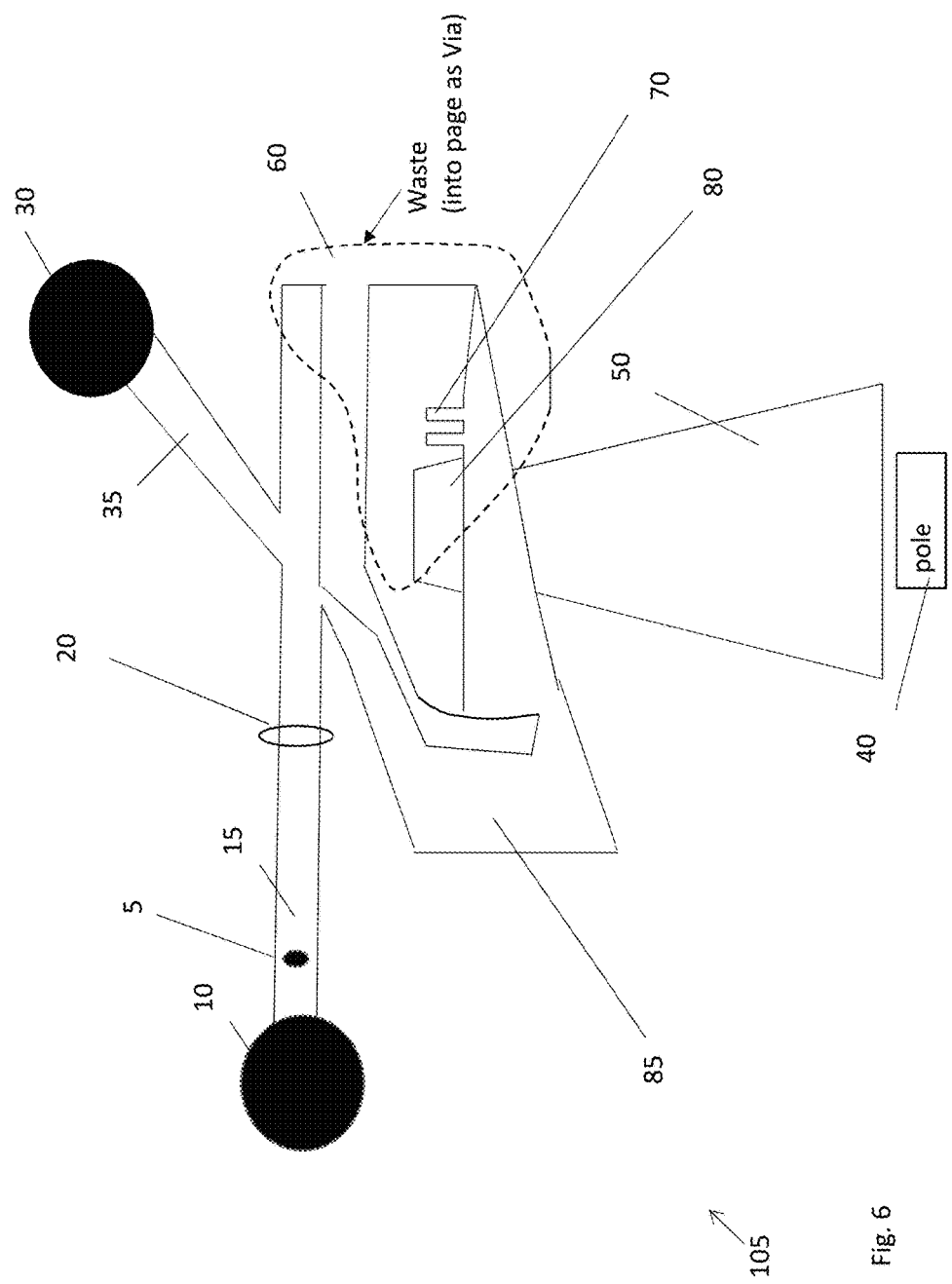
FIG. 6 is a schematic illustration of a particle manipulating structure wherein the waste channel is a vertically opening cavity, and which does not need to be armed.

FIG. 6 is a schematic plan view of another embodiment 105 of the pressure sorting device. A distinguishing feature of the embodiment 105 is that the movable member 80 is in direct fluid communication with a large reservoir of fluid, and thus there is relatively little hydrodynamic resistance to its movement.

In FIG. 6, the sample stream is again input at input reservoir 10, and travels down the input channel 15, to the laser query region 20. The sample stream may contain target particle 5, as well as non-target material. At the query station 20, if a signal is detected that corresponds to a target particle 5, a computer will give a signal to sort that particle 5. Upon the signal, and electromagnet (not shown) is energized causing magnetic flux to exit the pole 40 and enter the permeable feature 50. Although not explicitly shown, it should be understood that the movable member 80 may have a permeable magnetic material 130 inlaid into the member 80, causing it to be responsive to magnetic flux, as was previously described with respect to FIGS. 1a and 1b. Because of the magnetization existing in the permeable feature 50, the movable member 80 is pulled toward the permeable feature 50, this forces a volume of fluid to be pushed out of the pressure channel 85 by the movable member 80 and into the sort channel 35. This pulse of higher pressure fluid may cause the target particle 5 to be deflected into the sort channel 35 and eventually into the sort reservoir 30. When the movable member 80 is not deflected, the target particle will pass through unimpeded to the waste channel 60.

In this embodiment 105, the waste channel 60 may be disposed out of the plane of the sort channel 35 and input channel 15. The movable member 80 may be in immediate fluid communication with the waste channel 60, because the structure and its movement may overlap the mouth of the opening 60, as shown in FIG. 6. Accordingly, because the waste channel is a large vertical channel attached to the output of the channel, it may have exceedingly low resistance to the flow. Since the movable member 80 is in fluid communication with the waste channel 60, and its resistance to the movement of the movable member 80 may be minimal. To emphasize the dimensions and placement of the waste channel 60, it is shown in textured stippling in FIGS. 6 and 7.

The embodiment 105 shown in FIG. 6 is a normally open device, which when the movable member 80 is pulled toward the permeable feature 50, cause a pulse of high-pressure fluid to be forced into the input channel 15. Accordingly, when a target particle 5 is detected in the laser query region 20, and after an interval of time is deemed to be at the intersection of the sort channel 35 and the waste channel 65, the electromagnet 400 may be energized, causing a transient, high pressure fluidic pulse to be created at this intersection. This pressure pulse may drive the target particle 5 into the sort channel 35.

Figure 7:
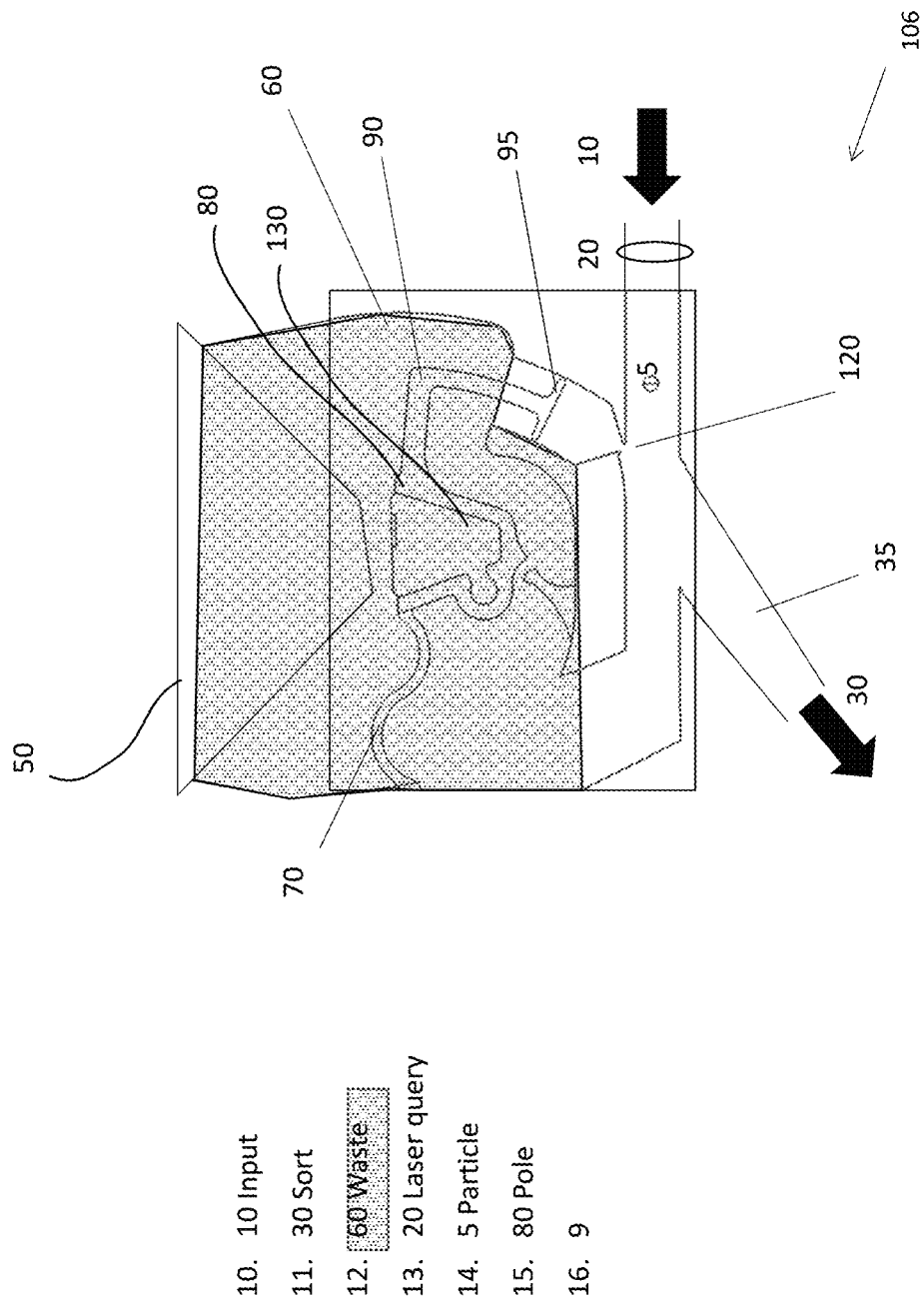
FIG. 7 is detail of another particle sorting system which sorts particles using a pulse of fluidic pressure.

FIG. 7 is a schematic illustration in the plan view of another exemplary embodiment 106 of this novel device. A distinguishing feature of the embodiment 106 is the use of a lever, or arm and a jet-forming nozzle, to increase the throw of the movable member 80 therefore increasing the acting force on the target particle.

In FIG. 7 once again, the input reservoir is 10, the sort reservoir is 30, and the waste reservoir is 60. An input stream is input at the input orifice 10, and travels down the input channel 15 past a laser query zone 20. The target particle 5 and stream continue on towards the waste channel 60 via the waste channel 65. If a target particle 5 is detected in the laser query zone 20, a computer will give a signal to sort that particle, 5. Upon the signal, an electromagnet (not shown) may be de-energized, causing magnetic flux to dissipate from the permeable pole piece 50. Because of the de-magnetization of the pole piece 50, the movable member 80 is released from the pole 50 and returns to the as-manufactured position, forcing a volume of fluid to be pushed out of the piston area and into the input channel 15. This pulse of higher pressure fluid causes the target particle 5 to be deflected into the sort channel 35 and eventually into the sort reservoir 30. When the movable member 80 is not deflected, the target particle will pass through unimpeded to the waste channel 60.

The electromagnetic actuator mechanism of embodiment 106 may be comprised of a permeable feature 130 that is inlaid into the movable structure 80. The movable structure 80 may have piston-like structure 95 connected to it by an arm 90. This arm 90 may give the piston 95 more throw, or range of motion than prior embodiments. This additional throw may increase the strength or the volume of pressurized fluid injected into the pressure channel 85 therefore increasing the velocity of induced jet.

The movable structure 80 may be configured as an arm 90 and a piston 95 in a rather tightly fitting channel or tube 97 (see FIG. 8). The piston 95 forces liquid into nozzle 120 located at the end of the tightly fitting channel or tube 97. As the fluid is compressed by the piston 95, the pressure in the fluid increases, and it is forced to the nozzle 120 into a puff of high-pressure fluid into the pressure channel 85. This pressure may force a target particle 5 floating in the input stream to be forced into the sort channel 35, and then into the sort reservoir 30.

The embodiment 106 shown in FIG. 7 is similar to the embodiment shown in FIG. 5, in that the waste channel 60 is a vertical channel formed in an underlying substrate. Additional details of this orthogonal geometry are set forth in U.S. Pat. No. 9,372,144 issued Jun. 21, 2016, which is hereby incorporated by reference in its entirety.

FIG. 8 shows embodiment 106 of FIG. 7 in more detail. In FIG. 8, the input channel is 10, the sort channel is 30, and the waste channel reservoir is 60. An input stream is input at the input orifice 10, and travels down the input channel 15 passed a laser query zone 20. The target particle 5 and stream continue on towards the waste channel reservoir 60 via the waste channel 65. If a target particle 5 is detected in the laser query zone 20, a computer will give a signal to sort that particle, 5. Upon the signal, an electromagnet (not shown) is de-energized causing magnetic flux to dissipate from the permeable pole piece 50. Although not explicitly shown, it should be understood that the movable member 80 may have a permeable magnetic material 130 inlaid into the member 80, causing it to be responsive to magnetic flux, as was previously described with respect to FIGS. 1a and 1b. Because of the magnetization dissipating from the pole piece 50, the movable member 80 is released from the pole 50, this forces a volume of fluid to be pushed out of the nozzle area 2 and into the sort channel 35. This pulse of higher pressure fluid causes the target particle 5 to be deflected into the sort channel 35 and eventually into the sort reservoir 30. When the movable structure 80 is not deflected, the target particle will pass through unimpeded to the waste channel 65.

In many embodiments, a restoring spring 70 may be used to return the movable member 80 to its unactuated position. That is, when the actuating force or mechanism is quiescent, a force may be needed to return the movable member 80 to its original position. A restoring spring 70 may be an isthmus of substrate material that is left after the formation of the movable member. If the substrate material is single crystal silicon, the restoring spring 70 also could be single crystal silicon. As a result, the spring may still be made quite narrow yet stiff, because of the outstanding mechanical properties of this material. Other types of restoring springs may be used, however, or the movable member may be returned to its original position by the application of a force by a force generating mechanism in the opposite direction.

Once again, the electromagnetic actuator mechanism may comprise a permeable feature 130 that is inlaid into the movable structure 80. The movable structure 80 may be configured as a piston 95 in a rather tightly fitting channel or tube 97, and connected to the movable member 80 by an arm 90. The piston 95 may force liquid into nozzle 120 located at the end of the tightly fitting channel or tube 97. As the fluid is compressed by the piston 95, the pressure in the fluid increases, and it is forced out of the nozzle 120 in a pulse of high-pressure fluid. The fluid may be ejected into the input channel 15. This pressure may force a target particle 5 floating in the input stream into the sort channel 35, and then into the sort reservoir 30.

As shown in FIG. 8 an angle may exist between the axis of the piston 95 and the midline of the inlet channel 15. This angle as shown in the diagram as reference number three (3). This angle may have a critical effect on performances and will be discussed later with respect to FIG. 9. Accordingly, it should be noted that the passages in this novel device are not generally orthogonal to the sample inlet channel and/or the waste channel. As discussed below, this non-orthogonal angle may be an important design choice and may affect the overall operation of the device in an advantageous way, as discussed further below.

Another important parameter is the opening dimension for the nozzle 120. A larger opening may increase the volume of pressurized fluid, but decrease the pressure and reduce the tightness of the jet being emitted. The microfabricated input channel and sort channel may be on the order of about 20 microns to about 50 microns, wide enough to admit cell-sized particles generally in single file.

In one exemplary embodiment, the piston width 1 is about 30 microns, the nozzle width 2 is about 4 microns, the nozzle angle 3 is about 45 degrees, and the channel widths (inlet channel and sort channel) are about 50 microns.

FIG. 9 shows modeled details of flow inside the pressure channel as nozzle 120 produces a transient pulse of pressure. In FIG. 9a, the piston is just beginning to push fluid out of the nozzle 120. In FIG. 9b, the maximum transient pressure is being generated, urging the target particle 5 towards the mouth of the sort channel 35. In FIG. 9c, the pressure pulse has largely dissipated, and the target particle 5 is well into the sort channel 35. In FIG. 9c and afterwards, the flow returns to its relatively unperturbed state, with the sample stream flowing 80% into the waste channel and about 20% into the sort channel, as will be described next.

One of the effects observed in the transient pressure sorter is that the application of pressure from the actuator injects pressurized fluid into the sort channel. This fluid pressure is transmitted throughout the sort, sample and waste channels, and causes a slowdown in the velocity of the flow at the input channel, because it acts generally against this flow. This transient effect causes uncertainty in the flow rate down the channel, which affects the timing of when target particle 5 reaches the sorting area and therefore the transient effect causes uncertainty in the sorting. Accordingly, the action of the transient pressure pulse—from any source—may cause a deterioration in the purity or yield of the sorting device or the sorting rate with which the device may be operated.

Figure 10B:
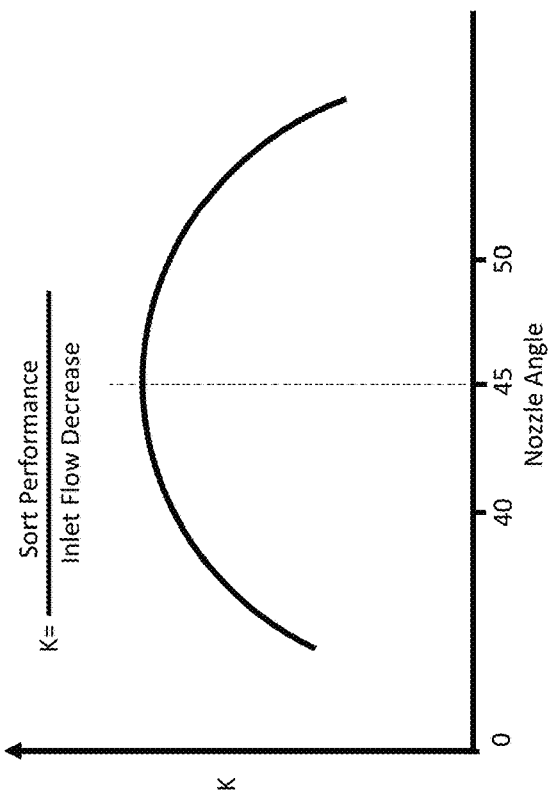
FIG. 10b shows the functional dependence of performance vs. nozzle angle.
Figure 10A:
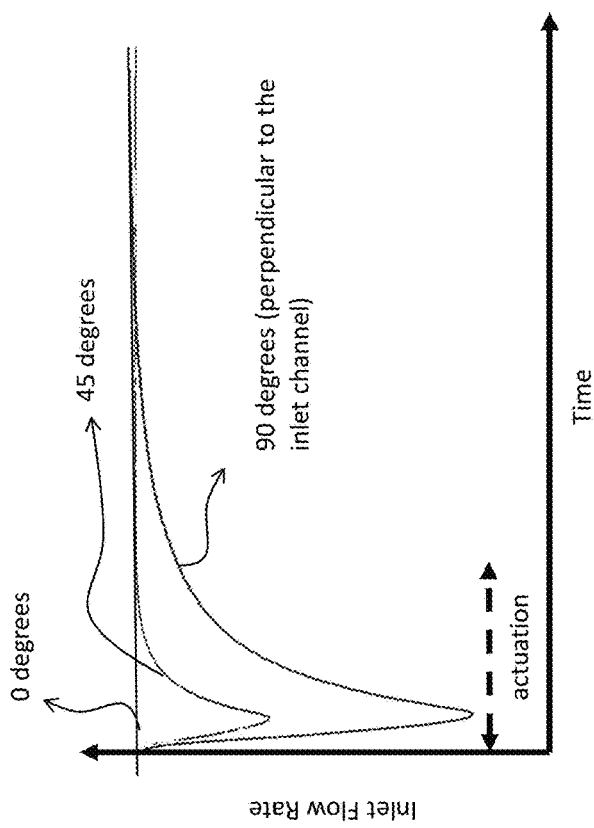
FIG. 10a is a plot of the deviation of the inlet flow rate as a function of nozzle angle

FIGS. 10a and 10b illustrate this effect. FIG. 10a shows a plot of the deviation of the input flow rate as a function of nozzle angle. As the high flow rate jet exits the nozzle, the pressure may counter the flow in the channel, slowing the velocity of flow at the laser query zone 20 and nozzle region 120. In other words, the input flow rate may decrease as the jet actuates and the amount of decrease may depend on the nozzle angle. Because of this change in the flow rate, the velocity of the target particle 5 in the sample channel 15 has more uncertainty. This adds uncertainty to the timing of the subsequent particles, and thus limits the rate with which the particles can be sorted. As one can see in FIG. 10a, the magnitude of the perturbation depends on the angle that the nozzle makes with respect to the channel. At an angle of 90 degrees (orthogonal), the perturbation is profound. At 45 degrees, the perturbation is about 3-5× reduced. Smaller nozzle angles perturb the inlet flow less. Therefore, the velocity measurement for the cell that is sorted next will be more accurate. However, at 0°, it is impossible to sort the target particle 5, because there is no distinctive flow channel into which the sorted particle can go. In other words, the sort channel is the same as the waste channels, so sorting is not possible, or at least the sort purity may become badly deteriorated as the angle becomes shallower. It should be noted that using a push-pull configuration, it may be possible to reduce the perturbation of the input fluid flow rate to nearly zero, because the slow down due to the pushing member may be offset by the speedup due to the pulling member.

An optimization study reveals that the optimum performance is achieved at around 45 degrees nozzle angle. At higher angles, the flow rate perturbation becomes larger, degrading the sort accuracy. At lower angles, the effective force driving the target particle to the sort channel decreases. Also the sort accuracy diminishes because unintended particles can inadvertently flow into the sort channel. FIG. 10b illustrates the functional dependence on the angle between the sort channel, and the sample input and waste channels. As illustrated in FIG. 10b, there is an optimum angle of about 45 degrees, wherein the pressure perturbation of the flow channel is minimized, and thus the effectiveness of the pressure pulse is maximized. The useful range may be between about 30 and about 60 degrees, but with an optimum at about 45 degrees.

Accordingly, nozzle angle may affect both the inlet flow perturbation and sorting efficiency. As the angle becomes smaller, the jet is less effective and may not be able to push the target particle 5 to the sort channel. As a result, there may be an optimum value for the nozzle angle which may be about 45 degrees.

Figure 11:
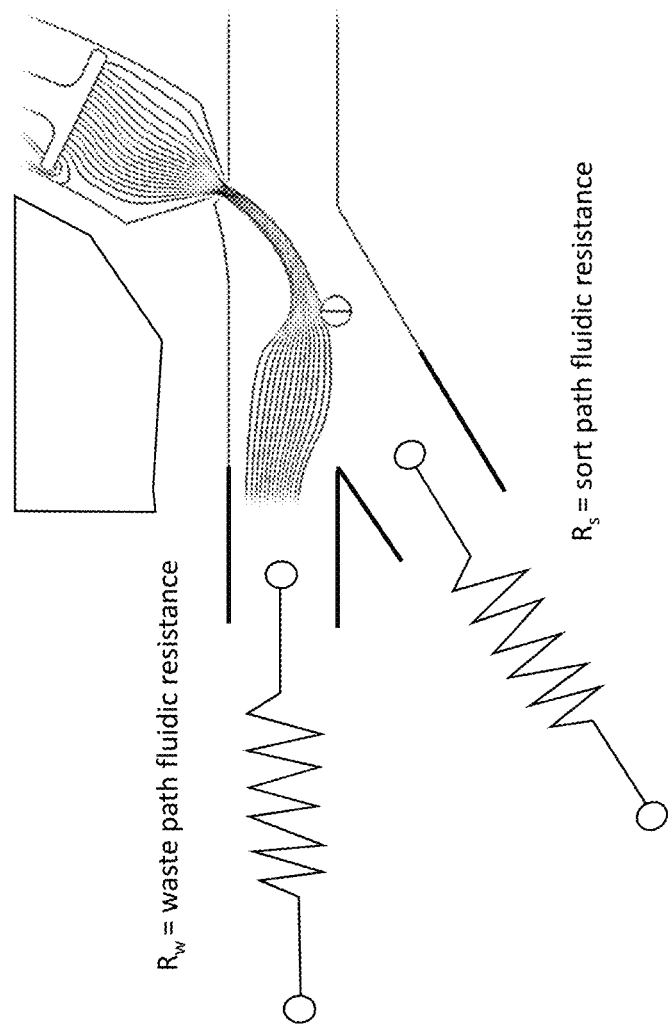
FIG. 11 is a schematic illustration of the importance of the relative fluidic resistance of the sort path versus the waste path.

FIG. 11 is a schematic illustration showing the relative flow rates, i.e. the relative resistance of the path to the flow of the fluid, between the exit channels downstream of the sort mechanism. In FIG. 11, the horizontal channel is the waste path, and the angled channel is the sort path. As can be seen, there is an angle between the waste/inlet path and the sort path, which was previously discussed. However, another important design consideration is the fluidic resistance of one path relative to the other. More specifically, the fluid resistance of the sort path should be some multiple of the fluidic resistance of the waste path. In fact, it has been shown that the ratio of the sort path fluidic resistance to the waste path resistance should be a number on the order of 5. With a significant flow into the channel, a relatively modest transient pressure pulse can cause the target particle 5 to flow into the sort channel. That is, resistance to flow in the sort channel should be on the order of 5× greater than resistance to flow in the waste path, such that 5× more fluid flows into the waste path than into the sort path. Accordingly, in some embodiments, 20% of the flow may go into the sort channel, with 80% proceeding into the waste channel, in general. If the flow into the sort channel is too low, the pressure pulse is ineffective at moving the target particle into the sort channel.

It may be important to have the right ratio of sort path fluidics resistance $R_s$ and waste $R_w$. In another embodiment, the ratio for these quantities $R_s/R_w$ may be on the order of 5. Too much flow down the sort path will result in unwanted particles traveling to the sort reservoir (even without actuation) and too much resistance in the sort path will render the transient pressure pulse sorting ineffective.

The sorting devices 10, 100, 101, 102, 103, 104, 105 and 106 may all be made using similar lithographic processes. The permeable inlaid feature may be, for example, nickel iron Permalloy (50-80% Ni and 40-20% Fe) which may be plated into an indentation etched out of the surface of the substrate. If the inlaid material 130 is over-plated (plated beyond the level of the surface of the substrate), it may then be polished flat by chemical mechanical polishing, for example.

The movable member 80 and 82 may be made by deep reactive ion etching through the device layer of an silicon-on-insulator (SOI) substrate. The movable structure may be freed by etching away the silicon dioxide layer beneath the etched outline. Microfluidic channels may be formed in the device layer as well using DRIE. The channels may be sealed with a roof of an optically transparent material such that the laser excitation may be delivered to the laser query regions 20. Borosilicate glass may be an acceptable transparent material to cover the microfabricated inlet, sort and waste channels.

Because the movable member 80 and 82 may be made from the device layer of an SOI substrate, these structures may comprise single crystal silicon, which has exceedingly advantageous mechanical characteristics. Included among these features are very high rigidity, high stiffness, and low creep. This material may be especially advantageous for the formation of the restoring spring 70 and 75, which may attach the movable member 80 to the remaining substrate. This spring 70 and 75 may be made exceedingly thin and flexible, yet highly reliable in terms of resistance to breakage and creep.

The vertical waste channels 60 may be made by forming a hole in an additional substrate, and gluing the additional substrate to the SOI wafer. Additional details as to the fabrication of these devices may be found in U.S. Pat. No. 9,372,144 issued Jun. 21, 2016.

A microfabricated particle sorting device is described, which is fabricated on a substrate, and may separate a target particle from non-target material flowing in a fluid stream. The particle separation device may include a detection region which generates a signal distinguishing the target particle from non-target material, a sample inlet channel, a sort channel and a waste channel also fabricated on the same substrate, wherein the target particle is urged into the sort channel rather than the waste channel by a transient pulse of fluidic pressure; wherein the pulse of pressure is generated by an actuator fabricated on the same substrate as the sample inlet channel.

The transient pulse may have a higher pressure than the surrounding fluid, and wherein the higher pressure pushes the target particle into the sort channel. Alternatively, the transient pulse may have a lower pressure than the surrounding fluid, and wherein the lower pressure pulls the target particle into the sort channel. Alternatively, the transient pulse may have a higher pressure in one location and a lower pressure in another location, than the surrounding fluid, wherein the higher pressure and the lower pressure direct the target particle into the sort channel. The transient pulse may be generated at the tip of a tapered nozzle formed in the substrate, and wherein the tapered nozzle and the sort channel are disposed at a non-orthogonal angle with respect to the waste channel, and disposed across the waste channel with respect to one another, and downstream of a laser interrogation region. The angle may be between 30 and 60 degrees.

The actuator may operate based on at least one of electrostatic, electromagnetic and piezoelectric forces. The waste channel may be disposed substantially orthogonally to a plane that contains the sort and the sample inlet channel. The tapered nozzle may have a width between about 3 microns and 15 microns. The fluid stream may be diverted to the sort channel as the actuator is released into a quiescent state (normally on). The fluid stream may be diverted to the sort channel as the actuator is driven from a quiescent state to an actuated state (normally off). the sample inlet stream may flow to the sort channel with the actuator in the quiescent state (normally on).

The actuator is actuated by electromagnetic forces arising between an external electromagnet and a permeable material inlaid into a movable member. The movable member may move in response to the energizing of the external electromagnet, and move in the plane that also contains the sample inlet channel and the sort channel. is actuated by electromagnetic forces arising between an external electromagnet and a permeable material inlaid into the movable member.

The movable member may be solidly connected to the substrate with an isthmus of substrate material remaining after formation of the movable member, wherein this isthmus of substrate material provides restoring force to return the movable member to its original position when the electromagnet is de-energized. The movable member may be disposed over the waste channel over at least a portion of its movement, such that a passage exists for the target particle to flow from the sample inlet channel to the waste channel with the movable member in a predefined position in the plane.

The detection region may be a laser interrogation region, wherein laser radiation is applied to the sample stream. The sample stream may include suspended target particles which are tagged with a fluorescent tag that interacts with the laser radiation to emit an identifying optical signal. The detection region may measure at least one of a mechanical, optical, electrical, magnetic or chemical property of the target particle, to distinguish the target particle from non-target material. The external electromagnetic may have a coil wrapped around a single permeable core having a north pole and a south pole, with magnetic flux emanating from the north pole, going through space and returning to the south pole of the permeable core.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A microfabricated particle sorting device fabricated on a substrate, that separates a target particle from non-target material flowing in a fluid stream, the particle separation device comprising:
   a detection region which generates a signal distinguishing the target particle from non-target material;
   a sample inlet channel, a sort channel and a waste channel also fabricated on the same substrate, wherein the target particle is urged into the sort channel rather than the waste channel by a transient pulse of fluidic pressure; wherein the pulse of pressure is generated by an actuator fabricated on the same substrate as the sample inlet channel, wherein the transient pulse has a higher pressure in one location and a lower pressure in another location, than the surrounding fluid, wherein the higher pressure and the lower pressure direct the target particle into the sort channel.

2. The microfabricated particle sorting device of claim 1, wherein the transient pulse has a higher pressure than the surrounding fluid, and wherein the higher pressure pushes the target particle into the sort channel.

3. The microfabricated particle sorting device of claim 1, wherein the transient pulse has a lower pressure than the surrounding fluid, and wherein the lower pressure pulls the target particle into the sort channel.

4. The microfabricated particle sorting device of claim 1, wherein the transient pulse is generated at the tip of a tapered nozzle formed in the substrate, and wherein the tapered nozzle and the sort channel are disposed at a non-orthogonal angle with respect to the waste channel, and disposed across the waste channel with respect to one another, and downstream of a laser interrogation region.

5. The microfabricated particle sorting device of claim 1, wherein the transient pressure pulse is applied at an angle to a centerline of the sample stream, and the angle is between 30 and 60 degrees.

6. The microfabricated particle sorting device of claim 1, wherein the actuator operates based on at least one of electrostatic, electromagnetic and piezoelectric forces.

7. The microfabricated particle sorting device of claim 1, wherein the waste channel is disposed substantially orthogonally to a plane that contains the sort and the sample inlet channel.

8. The microfabricated particle sorting device of claim 4, wherein the tapered nozzle width is between 3 microns and 15 microns.

9. The microfabricated particle sorting device of claim 1, wherein the fluid stream is briefly diverted to the sort channel as the actuator is released into a quiescent state.

10. The microfabricated particle sorting device of claim 1, wherein the fluid stream is briefly diverted to the sort channel as the actuator is driven from a quiescent state to an actuated state.

11. The microfabricated particle sorting device of claim 1, where in the sample inlet stream flows to the sort channel with the actuator in the quiescent state.

12. The microfabricated particle sorting device of claim 1, where in the actuator is actuated by electromagnetic forces arising between an external electromagnet and a permeable material inlaid into a movable member.

13. The microfabricated particle sorting device of claim 12, wherein the movable member moves in response to the energizing of the external electromagnet, and moves in the plane that also contains the sample inlet channel and the sort channel is actuated by electromagnetic forces arising between an external electromagnet and a permeable material inlaid into the movable member.

14. The microfabricated particle sorting device of claim 13, wherein the movable member is solidly connected to the substrate with an isthmus of substrate material remaining after formation of the movable member, wherein this isthmus of substrate material provides restoring force to return the movable member to its original position when the electromagnet is de-energized.

15. The microfabricated particle sorting device of claim 14, where in the movable member is disposed over the waste channel over at least a portion of its movement, such that a passage exists for the target particle to flow from the sample inlet channel to the waste channel with the movable member in a predefined position in the plane.

16. The microfabricated particle sorting device of claim 1, wherein the detection region is a laser interrogation region, wherein laser radiation is applied to the sample stream.

17. The microfabricated particle sorting device of claim 16, wherein the sample stream includes suspended target particles which are tagged with a fluorescent tag that interacts with the laser radiation to emit an identifying optical signal.

18. The microfabricated particle sorting device of claim 1, wherein the detection region measures at least one of a mechanical, optical, electrical, magnetic or chemical property of the target particle, to distinguish the target particle from non-target material.

19. The microfabricated particle sorting device of claim 12, wherein the external electromagnetic having a coil wrapped around a single permeable core having a north pole and a south pole, with magnetic flux emanating from the north pole, going through space and returning to the south pole of the permeable core.

* * * * *